United States Patent [19]
Taniji et al.

[11] Patent Number: 5,291,885
[45] Date of Patent: Mar. 8, 1994

[54] APPARATUS FOR MEASURING BLOOD FLOW

[75] Inventors: Ayafumi Taniji; Muneharu Ishikawa, both of Tsukuba, Japan

[73] Assignee: Kowa Company Ltd., Japan

[21] Appl. No.: 795,814

[22] Filed: Nov. 21, 1991

[30] Foreign Application Priority Data

Nov. 27, 1990 [JP] Japan .................... 2-320640

[51] Int. Cl.$^5$ .............................................. A61B 5/00
[52] U.S. Cl. ................................. 128/633; 128/634
[58] Field of Search ......................... 128/632–634; 351/205, 221

[56] References Cited

U.S. PATENT DOCUMENTS

| | | | |
|---|---|---|---|
| 4,423,932 | 1/1984 | Takahashi | 351/221 |
| 4,579,430 | 4/1986 | Bille | 128/633 |
| 4,679,917 | 7/1987 | Genco et al. | 351/221 |
| 4,768,874 | 9/1988 | Webb et al. | 351/221 |
| 4,773,097 | 9/1988 | Suzaki et al. | 128/633 |
| 4,838,679 | 1/1989 | Bille | 351/221 |
| 4,848,897 | 7/1989 | Aizu et al. | 351/221 |
| 4,854,693 | 8/1989 | Ichihashi et al. | 128/633 |
| 4,867,554 | 9/1989 | Matsumura | 351/205 |
| 4,952,049 | 8/1990 | Matsumoto | 351/205 |
| 4,991,953 | 2/1991 | Pflibsen et al. | 351/221 |
| 5,072,731 | 12/1991 | Taratuta et al. | 128/633 |
| 5,139,022 | 8/1992 | Lempert | 351/221 |
| 5,177,511 | 1/1993 | Feuerstein et al. | 351/205 |

*Primary Examiner*—Randall L. Green
*Assistant Examiner*—Gina M. Gaultieri
*Attorney, Agent, or Firm*—Bruce L. Adams; Van C. Wilks

[57] ABSTRACT

An apparatus for measuring blood flow in which an optical system guides a coherent light beam to impinge on a stationary measurement spot of a measurement plane of an in vivo tissue. A light-receiving optical system focuses a light image of the measurement plane in the vicinity of an image point conjugate with the stationary measurement spot. The light-receiving optical system shares at least part of the optical components of the guiding optical system. Photodetectors are disposed at prescribed positions perpendicular to the optical axis of the light-receiving optical system, and in the vicinity of the image point, for measuring light scattered from the in vivo tissue to provide blood flow information. The blood flow information is related to blood flowing at a depth within the in vivo tissue. A visible image of the measurement plane is converted into a video image. The blood flow information corresponding to the position of the stationary measurement spot is superimposed on the video image and displayed to obtain a composite visible image.

9 Claims, 4 Drawing Sheets

SCANNING SPOT

ERYTHROCYTE

PRIOR ART ns APPARATUS FOR MEASURING BLOOD FLOW

BACKGROUND OF THE INVENTION

1. Field of the Invention

This invention relates to an apparatus for measuring blood flow, and more particularly to an apparatus for noninvasively obtaining blood flow information within in vivo tissue while providing the capability to superimpose the blood flow information on a video image of the tissue to obtain a composite visible image.

2. Description of the Prior Art

Laser Doppler apparatuses or laser speckle apparatuses have ben marketed as apparatuses for noninvasively obtaining information on blood flow. These apparatuses measure blood flow factors by directing a laser beam into the blood steam, picking up light scattered by erythrocytes moving in the blood, and analyzing the frequency spectrum of the received light for determining the frequency gradient. An apparatus based on this method is disclosed, for example, in Japanese Patent Public Disclosure Sho 60(1985)-203235.

Such conventional apparatuses use a laser beam projecting probe and a light receiving probe, both constituted of optical fibers, and the measurement depths within the in vivo tissue is regulated by adjusting the distance between the probes (See Fujii et al., Measurement of blood flow in skin using laser beam phenomenon (V) (Japan Laser Medical Magazine), Vol. 6, No. 3 (January 1986)).

An example of the arrangement used is shown in FIG. 4. A laser beam is directed into in vivo tissue P from an optical fiber F1 and the scattered light is received by an optical fiber F2. The intensity of the light received by the light receiving fiber F2 is governed by its distance from the beam projecting fiber F1.

Assuming the tissue to be a perfect light scattering body, Fujii et al. approximated the intensity of the light received by the light receiving fiber F2 as shown below (Fujii et al., Evaluation of skin blood flow using laser speckle phenomena (VII) (The Journal of Japan Society for Laser Medicine), Vol. 7, No. 3 (January 187)).

$$Im = I_0 \, Exp\{-\gamma(R1+r2)\} \quad (1)$$

where
- $Im$: intensity of received light
- $I_0$: intensity of irradiating beam
- $\gamma$: coefficient of attenuation owing to absorption and scattering
- $r1$: distance between end surface P1 of beam projecting fiber and light scattering particles (erythrocytes)
- $r2$: distance between end surface P2 of light receiving fiber and light scattering particles (erythrocytes)

This equation being that of an ellipse having its foci at the points P1 and P2 where the light enters and leaves the tissue, it can be seen that the length of the light path for which scattered light can be received increases with increasing distance between the points P1 and P2. In other words, scattered light from deeper parts of the tissue can be received by increasing the distance between the optical fibers F1 and F2.

As this conventional arrangement requires the optical fiber probes to be brought in contact with the tissue with respect to which measurement is being conducted, it is apt to have undesirable effects on the patient, such as making him or her feel uneasy or uncomfortable.

Scanning a large measurement region using the conventional arrangement involves the troublesome work of repeatedly repositioning the measurement probes and, moreover, requires the position information to be recorded after each repositioning. The measurement work is thus complicated and laborious.

SUMMARY OF THE INVENTION

An object of the present invention is therefore to provide an apparatus capable of obtaining blood flow information from a depth within in vivo tissue in a contactless manner without using optical fibers or the like, displaying while simultaneously a video image of the measurement region of the in vivo tissue, and capable of enabling positional information relating to a large measurement region of the in vivo tissue to be acquired simply and quickly during the measurement.

In accordance with the present invention, an apparatus for measuring a blood flow comprises a scanning optical system for scanning a measurement plane of an in vivo tissue in a desired pattern with a scanning spot formed by a coherent light beam so that the coherent light beam impinges on a stationary measurement spot of the in vivo tissue a light receiving optical system for focusing an image of the measurement plane in the vicinity of an image point conjugate with a scanning spot formed by the scanning optical system, the light receiving system sharing at least a part of the optical components of the scanning optical system, at least one photodetecting means disposed at prescribed positions in the vicinity of the image point for measuring light scattered from the in vivo tissue to provide blood flow information related to blood flowing at a depth within the in vivo tissue, video imaging means for receiving a visible image of the measurement plane and converting it into a video image, and image superimposing means for superposing information relating to the position of the scanning spot on the video image and displaying the video image and the blood flow information as a composite visible image.

Owing to these features, the apparatus for measuring blood flow according to the invention enables measurement of various data relating to blood flow at a depth within in vivo tissue to be carried out in a totally contactless manner, to be accomplished in respect of a large measurement region simply and at high speed while monitoring the measurement position on the visible image, and to be conducted without the need for mechanical positioning. In addition, it is structurally simple and inexpensive to manufacture.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
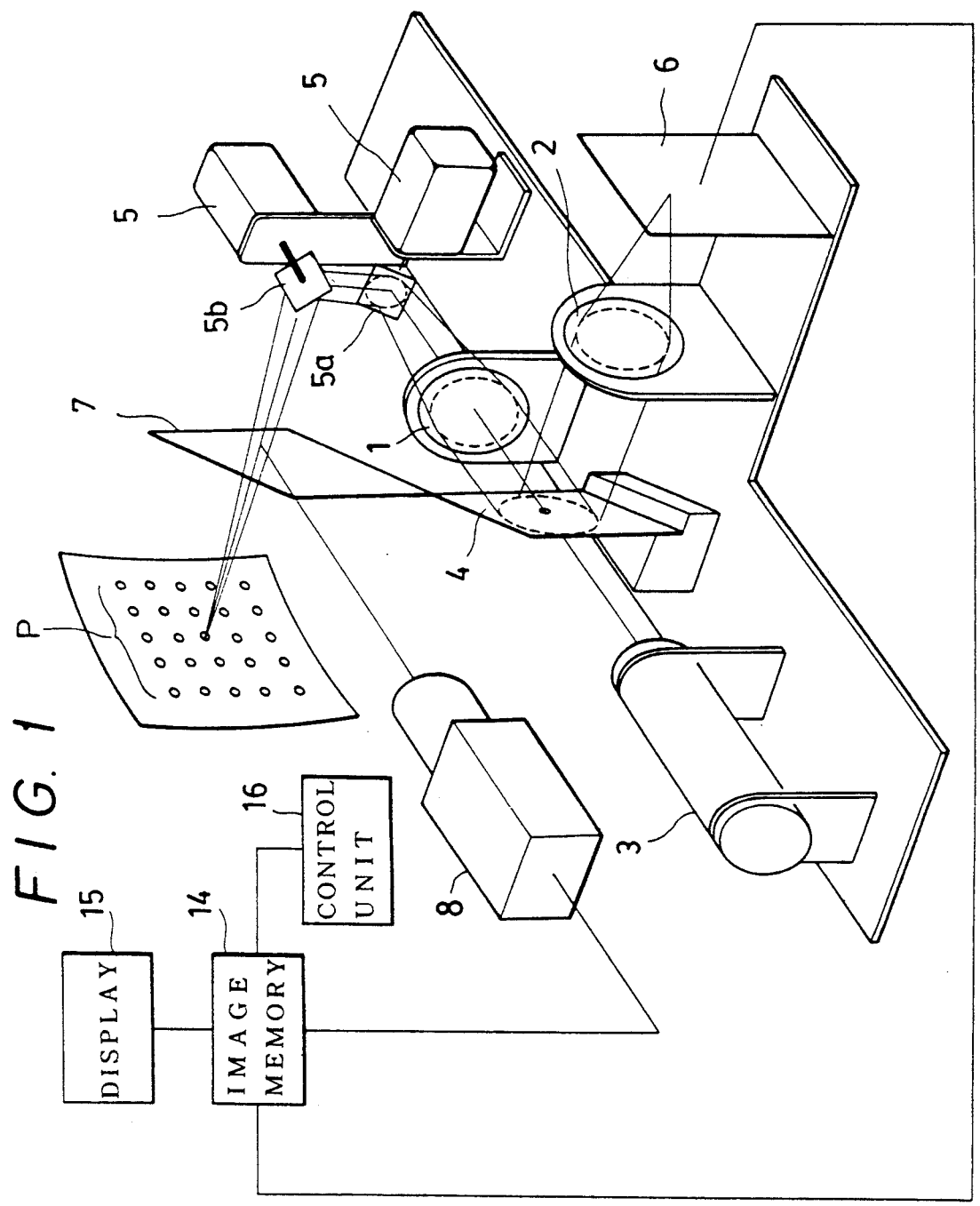
FIG. 1 is a perspective view of an apparatus for measuring blood flow in accordance with the present invention.

The invention will now be described in detail on the basis of the preferred embodiment illustrated in the drawings.

FIG. 1 shows the basic arrangement of the optical system of an apparatus for measuring blood flow embodying the present invention. A coherent light source such as a laser beam emitted by a laser beam source 3 passes through the center hole of a perforated mirror 4 and the center of a lens 1, is reflected in turn by mirrors 5a, 5b of a galvanoscanner 5 disposed for conducting two-dimensional scanning, and thus scans a measurement region P of in vivo tissue.

A laser beam source which emits a near infrared beam is used so as to minimize the amount of the laser beam light absorbed by the in vivo tissue. The measurement region P is further illuminated by white light from a source not shown in the figures.

A dichromatic mirror 7 disposed between the galvanoscanner 5 and the measurement region P transmits near infrared light and reflects light of other wavelengths toward a TV camera 8 so as to enable the TV camera 8 to pick up a visible image of the measurement region P.

The TV camera 8 transmits the picked-up measurement region P image (of non-near infrared light reflected by the dichromatic mirror 7) to an image memory 14 for synthesizing the visible image (picture) from the TV camera 8 and a light image obtained from a light receiving section 6 to be described later.

Since the in vivo tissue constituting the measurement region P is a light scattering body, it emits scattered light. The scattered light from blood corpuscles within the tissue blood vessels is partially scattered and partially absorbed by the tissue.

Figure 3:
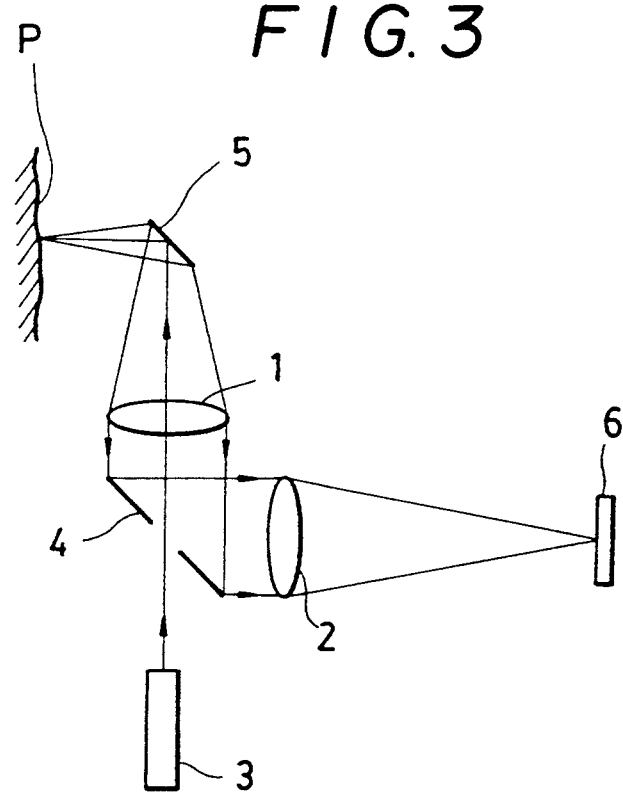
FIG. 3 is a plan view showing the positional relationship between an object and the light receiving plane (image plane)
Figure 4:
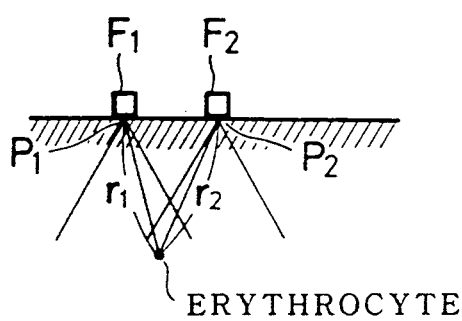
FIG. 4 is a diagram for explaining the conventional measurement method.

Light scattered by the tissue passes through the dichromatic mirror 7 and the lens 1 and is reflected by the perforated mirror 4 through a lens 2 to form a light image at a light-receiving or image plane of the light receiving section 6. The perforated mirror 4 is disposed between the lenses 1 and so as to prevent the laser beam from the laser beam source 3 from reaching the light receiving section 6. The image focusing system constituted by the lens 1, the lens 2 and the perforated mirror 4 is required to have a focal length that is large enough to avoid image blurring owing to oscillation of the mirrors 5a, 5b. For this purpose, therefore, the focal arrangement illustrated in FIG. 3 is established as regards the light receiving system at the focal plane and at the object surface. (The galvanoscanner 5 is represented schematically in FIG. 3.)

Figure 2:
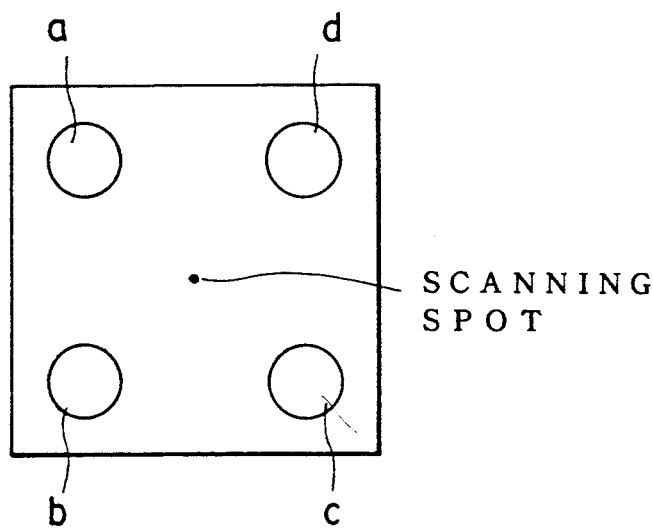
FIG. 2 is a schematic view for explaining the positional relationship between a scanning spot and photosensors within the light receiving plane (image plane) of the apparatus for measuring blood flow of FIG. 1.

An example of the arrangement of the light receiving section is shown in FIG. 2.

As shown in this figure, photosensors a-d are disposed at positions offset from the scanning spot. Differently from conventional apparatuses for measuring blood flows based on the laser speckle or laser Doppler principle, the apparatus for measuring blood flow according to this invention does not use optical fiber probes and, therefore, the depth of the measurement region is governed by the distance at the light receiving plane (image plane) between the scanning spot and the photosensors a-d, the numerical aperture of the lens 1 and the area of the sensors.

Placing sensors at four locations as shown in FIG. 2 makes it possible to receive information from a single scanning spot at four points and thus reduces the measurement time. The blood flow distribution can be measured at different depths by varying the distance between the scanning spot and the light receiving points and the so obtained information can be displayed on, for example, a display 15 in the manner described below.

Figure 5:
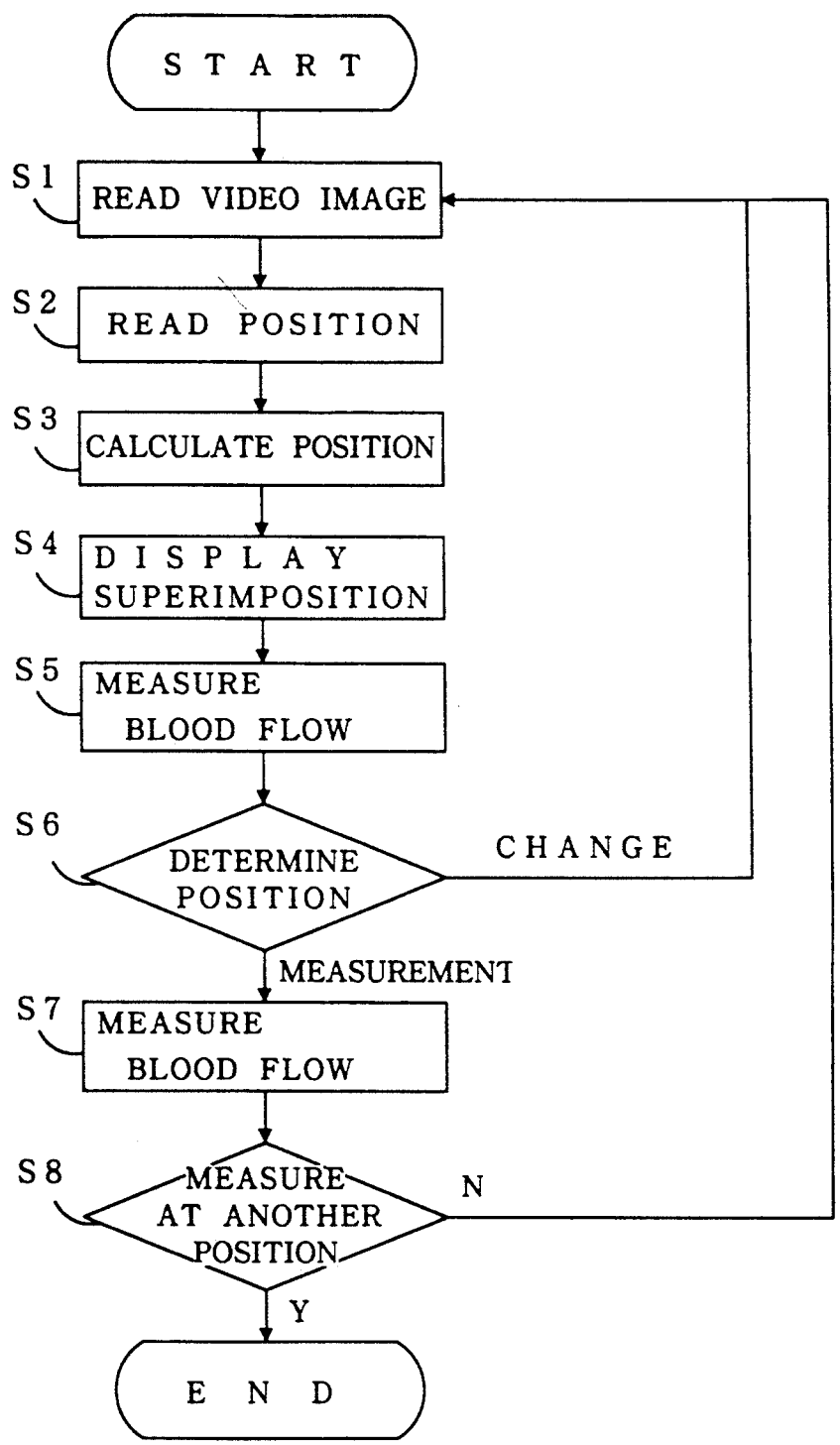
FIG. 5 is flowchart of procedures for image superimposition.

The video image (picture) output by the TV camera 8 and laser beam scanning position information obtained from the galvanoscanner 5 are synthesized in the image memory 14 in accordance with the procedures indicated in FIG. 5 and the result is output to the display 15.

The procedures of FIG. 5 are executed by a control unit 16 (constituted as a computer or the like) for overall control of the apparatus for measuring blood flow.

The procedure begins in step S1 in which the picture output by the TV camera 8 is read into the image memory 14. In the following step S2 the current laser beam scanning position is determined from position control information obtained from the galvanoscanner 5, whereafter a calculation is conducted in step S3 to determine what position within the picture output by the TV camera 8 the scanning position corresponds to.

The procedure then moves to step S4 in which, based on the result of the calculation in step S3, information indicating the current scanning position (in the form of a dot or the like) is superimposed on the TV camera picture in the image memory 14 and the result is displayed on the display 15. If a plurality of light receiving elements (photosensors) are disposed at the light receiving section 6 in the aforesaid manner, the corresponding positions are also displayed.

In the following step S5, blood flow data is measured in a manner to be explained later and, if desired, also superimposed on the TV camera picture appearing on the display 15.

The procedure then moves through steps S6 to S8 for controlling the scanning position, and if there is a change in the scanning position the procedures of steps S1 to S5 are repeated.

In such an arrangement, the beam (spot) of light output by the laser beam source 3 is deflected by galvanoscanner 5 so as to scan the measurement region P and scattered light from the measurement region P passes back through the lenses 1 and 2 of the scanning optical system to form a light image of the area in the vicinity of the scanning spot on the light receiving section 6. The four photosensors a-d disposed on the light receiving section 6 at prescribed distances from the light image of the scanning spot receive only that part of the scattered light reaching their respective positions. Using the variation in this scattered light as the main information regarding blood flow at the prescribed depth, it is then possible by analysis to determine the blood flow within the measurement region.

If a beam including light of more than one wavelength is used, the differences among the scattered amounts of the different wavelength lights can be analyzed as spectral information for determining the oxygen saturation at prescribed points within a given plane.

On the other hand, where a beam (spot) from a laser beam source is scanned in a prescribed manner and the dynamic spectral signals from the individual scanned points are analyzed, it becomes possible to determine the blood flow velocity distribution at a given depth within the in vivo tissue.

As methods for analyzing oxygen saturation and blood flow velocity are well known, only the basic principles will be discussed briefly here.

The oxygen saturation is determined from the amount of light the blood absorbs. Lambert-Beer's law defines the absorbance A of a solution in terms of incident light $I_{in}$ and transmitted light $I_{out}$ as $$A = \log(I_{in}/I_{out}) = ECL \quad (1)$$

where E is the absorbance coefficient at the wavelength of the light used, C is the substance concentration, $I_{in}$ is the amount of incident light, L is the length of the optical path and $I_{out}$ is the amount of transmitted light.

In the case of blood, since the absorbance is almost totally accounted for by hemoglobin, C in the aforesaid equation can be considered to be the hemoglobin concentration.

The coefficient of absorbance of hemoglobin varies with the saturation S and the wavelength as follows:

$$E = Er - S(Er - Eo)$$

where Er and Eo are the absorbance coefficients when S=0 and S=1, respectively.

Where $A_1$ and $A_2$ are the absorbances at wavelengths $\lambda 1$ and $\lambda 2$ $$A_1/Cl_1 = E_1 = Er_1 - S(Er_1 - Eo_1)$$

$$A_2/CL_2 = E_2 = Er_2 - S(Er_2 - Eo_2)$$

If the length of the optical path is the same for both wavelengths, $$L = L_1 = L_2$$

and, therefore, the absorbance ratio R for $\lambda 1$ and $\lambda 2$ can be expressed as $$\begin{aligned}R &= (A_1/A_2) \\ &= \{E_{r1} - S(E_{r1} - E_{o1})\}/\{E_{r2} - S(E_{r2} - E_{o2})\}\end{aligned}$$

The oxygen saturation S can therefore be expressed as $$S = \{E_{r1} = RE_{r2}\}/\{E_{r1} - E_{o1}) - R(E_{r2} - E_{o2})\}$$

whereby the oxygen saturation can be obtained from the ratio of the absorbances at two different wavelengths.

The oxygen saturation can therefore be determined by irradiating the tissue with light of two different wavelengths in the aforesaid manner.

Figure 6:
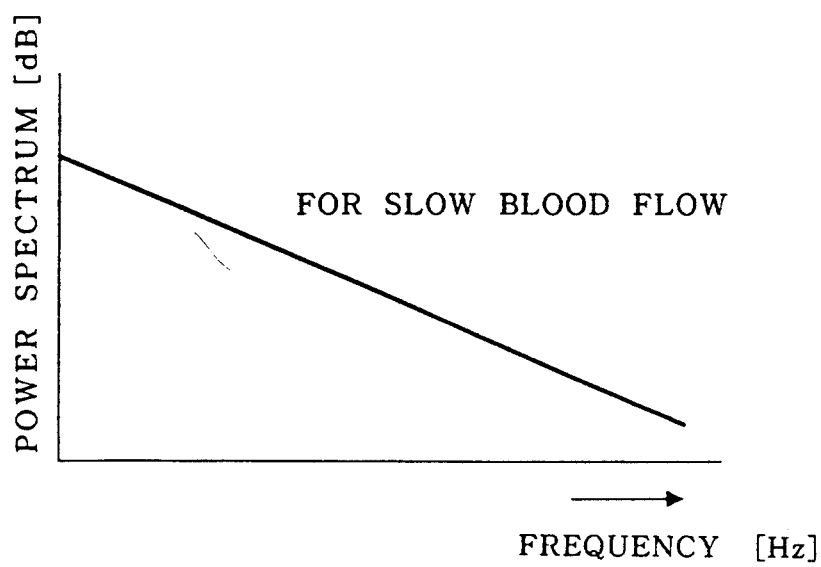
FIGS. 6a and 6b are graphs showing the qualitative relationship between blood flow velocity and the speckle intensity power spectrum.
Figure 6:
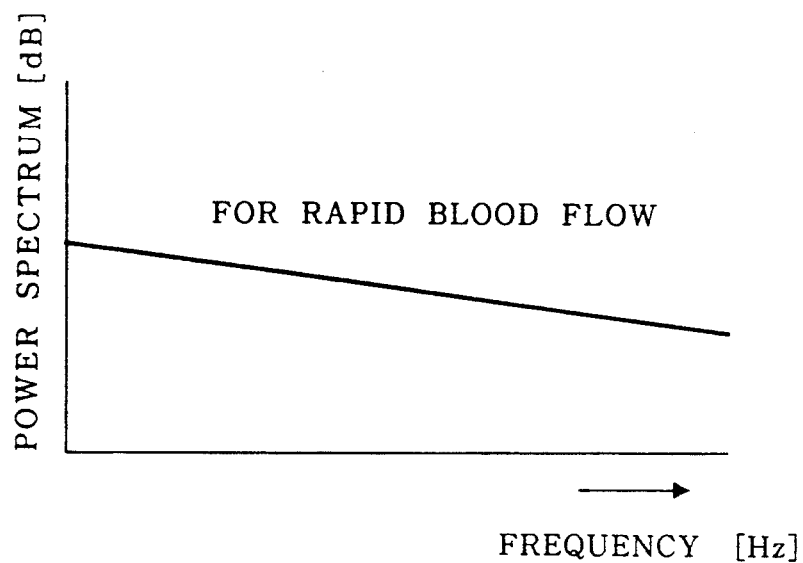

Blood flow velocity is measured by utilizing the fact that, when erythrocytes are irradiated by a laser beam, the frequency at which the intensity of the light scattered thereby varies is a function of their velocity. The light scattered by erythrocytes moving within an in vivo blood vessel forms what is referred to as a "boiling speckle" pattern. It is known that when the intensity variation of such speckles is frequency analyzed with respect to a given light receiving region on the tissue surface, the velocity of the erythrocytes is found to be related to the distribution of the power spectrum as shown in FIGS. 6a and 6b. When the erythrocyte velocity is high, the spectral distribution extends to higher frequencies. Taking advantage of this fact, the blood flow velocity is determined from the gradient of the power spectrum. Nohira, Shintomi, Ohura, Fujii, Asakura et al. determined blood flow velocity by finding the ratio of the absolute values of 40 Hz and 640 Hz signals. (See, for example, Evaluation of skin blood flow using laser speckle phenomena (III) and (IV), The Journal of Japan Society for Laser Medicine, Vol. 5, No. 3.)

In the present invention, since the galvanoscanner 5 is used both for scanning and as part of the light receiving system, the received light field is scanned simultaneously with the scanning spot. The embodiment of the invention described earlier, for example, is characterized in that the scanning spot and photosensors can, as a combined pair, be disposed for contactless scanning with the photosensors maintained in a fixed interval, whereby it becomes possible to position the measurement point while visually observing the measurement region on the display 15. With the beam projecting fiber and beam receiving fiber of the conventional apparatus for measuring blood flow referred to earlier, it is not possible to combine the measured results with measurement point position information, even by conducting measurement at a large number of points. In contrast, the apparatus for measuring blood flow according to the present invention is able to provide blood flow or oxygen saturation information including positional information.

Differently from conventional apparatuses of this type, it thus enables measurement while carrying out completely contactless positional scanning.

Moreover, once the object with respect to which measurement is to be conducted and the light receiving apparatus have been positioned, it becomes possible by laser beam scanning to carry out the measurement simply and quickly while visually observing a large measurement region. In the embodiment described in the foregoing the simultaneous measurement of scattered light data associated with a single scanning spot at four light receiving points (more if the number of sensors is increased) enables the measurement to be conducted at high speed.

In addition, since the scanning optical system and the light receiving optical system use some components in common, the apparatus becomes simpler in structure and, accordingly, less expensive to fabricate.

While in the embodiment set out in the foregoing the light receiving section was explained as having four photosensors disposed around the scanning spot at the center, the number of photosensors and their locations can be changed variously in line with the desired measurement depth and the like. It is also possible to constitute the photosensors of the light receiving section as a photomultiplier tube equipped with a mask for defining a plurality of light receiving positions. With this arrangement, the number of positions of the photosensors can be easily varied by using different masks.

While the invention has been described with reference to a preferred embodiment, it will be understood by those skilled in the art that various changes may be made and equivalents ay be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring a blood flow, comprising:
   a scanning optical system having optical components for guiding a coherent light beam to impinge on a stationary measurement spot of a measurement plane of an in vivo tissue;
   a light receiving optical system for focusing a light image of the measurement plane in the vicinity of an image point conjugate with the stationary measurement spot, the light image having an optical axis, and the light receiving optical system sharing at least a part of the optical components of the scanning optical system;
   at least one photodetecting means disposed at prescribed positions perpendicular to the optical axis and in the vicinity of the image point for measuring light scattered from the in vivo tissue to provide blood flow information related to blood flowing at a depth within the in vivo tissue;
   video imaging means for receiving a visible image of the measurement plane and converting it into a video image; and
   image superimposing means for superimposing blood flow information corresponding to the position of the stationary measurement spot on the video image and displaying the superimposed blood flow information and video image as a composite visible image.

2. An apparatus as st forth in claim 1, wherein the scanning optical system includes a galvanoscanner which is shared by the light receiving optical system and which produces the blood flow information corresponding to the position of the stationary measurement spot.

3. An apparatus as set forth in claim 1, further comprising light deflecting means disposed between the scanning optical system and the in vivo tissue for transmitting the wavelength of the coherent light beam to the light receiving optical system and for reflecting light of other wavelengths toward the video imaging means.

4. An apparatus as set forth in claim 1, wherein the position of the stationary measurement spot is displayed on the composite visible image.

5. An apparatus as set forth in claim 1, further comprising means for calculating oxygen saturation of blood at a depth within the in vivo tissue on the basis of the blood flow information.

6. An apparatus as set out in claim 1, further comprising means for calculating erythrocyte flow velocity distribution at a given depth within the in vivo tissue on the basis of the blood flow information.

7. A method for measuring blood flow and displaying blood flow information, comprising the steps:
   guiding a coherent light beam to impinge on a stationary measurement spot of a measurement plane of an in vivo tissue to obtain an image of the measurement plane of the in vivo tissue;
   focusing the image of the measurement plane of the in vivo tissue about an image point which corresponds to the stationary measurement spot;
   measuring coherent light scattered from the measurement plane of the in vivo tissue at the stationary measurement spot to obtain blood flow information related to flood flowing in the measurement plane of the in vivo tissue;
   forming a visible image of the measurement plane and converting the visible image into a video image;
   superimposing the blood flow information corresponding to the position of the stationary measurement spot on the video image; and
   displaying the superimposed blood flow information and video image as a composite visible image.

8. A method according to claim 7, wherein the guiding step is carried out by a coherent light beam composed of coherent light of different wavelengths; and the measuring step comprises measuring the amounts of coherent light of different wavelengths scattered from the measurement plane of the in vivo tissue at the stationary measurement spot to obtain spectral information indicative of oxygen saturation of the blood flowing in the measurement plane of the in vivo tissue.

9. A method according to claim 7, wherein the measuring step comprises measuring variation in the intensity of coherent light scattered from the measurement plane of the in vivo tissue at the stationary measurement spot to obtain blood flow information indicative of the blood flow velocity distribution at a given depth within the in vivo tissue.

* * * * *